United States Patent
Kick et al.

(10) Patent No.: US 7,699,864 B2
(45) Date of Patent: Apr. 20, 2010

(54) EXPANDABLE MEDICAL ACCESS DEVICE

(75) Inventors: George F. Kick, Casa Grande, AZ (US); Jay Lenker, Laguna Beach, CA (US); Onnik Tchulluian, Calrsbad, CA (US)

(73) Assignee: Onset Medical Corporation, Irvine, CA (US)

( * ) Notice: Subject to any disclaimer, the term of this patent is extended or adjusted under 35 U.S.C. 154(b) by 686 days.

(21) Appl. No.: 10/841,799

(22) Filed: May 7, 2004

(65) Prior Publication Data
US 2005/0222576 A1 Oct. 6, 2005

Related U.S. Application Data

(60) Provisional application No. 60/554,338, filed on Mar. 18, 2004.

(51) Int. Cl.
*A61M 29/00* (2006.01)
(52) U.S. Cl. .................. 606/198; 600/184; 604/104
(58) Field of Classification Search ......... 606/191–198, 606/213, 108; 604/506, 507, 264, 104, 109, 604/164.03; 600/201, 206, 208, 215, 219, 600/220, 224, 232, 233, 141, 142, 184
See application file for complete search history.

(56) References Cited

U.S. PATENT DOCUMENTS

| 702,789 | A |   | 6/1902 | Gibson |            |
|---------|---|---|--------|--------|------------|
| 3,788,318 | A | * | 1/1974 | Kim et al. | 604/164.3 |
| 3,789,852 | A | * | 2/1974 | Kim et al. | 604/104 |
| 4,601,713 | A |   | 7/1986 | Fuqua |             |
| 4,710,181 | A |   | 12/1987 | Fuqua |            |
| 4,738,666 | A |   | 4/1988 | Fuqua |             |
| 4,899,729 | A |   | 2/1990 | Gill et al. |         |
| 4,921,479 | A |   | 5/1990 | Grayzel |           |
| 4,960,122 | A | * | 10/1990 | Mizus | 128/207.14 |
| 5,092,839 | A |   | 3/1992 | Kipperman |         |
| 5,139,511 | A |   | 8/1992 | Gill et al. |        |

(Continued)

FOREIGN PATENT DOCUMENTS

EP 0 206 553 A1 12/1966

*Primary Examiner*—Anhtuan T Nguyen
*Assistant Examiner*—Kathleen Sonnett
(74) *Attorney, Agent, or Firm*—Knobbe, Martens Olson & Bear, LLP.

(57) ABSTRACT

An access device comprises a thin-walled sheath that is insertable into a patient through a small surgically created incision. The incision may be created using a cutdown or a percutaneous method such as that known as the Seldinger technique. Once inserted and advanced to the target surgical site, the sheath is selectively, and controllably, expanded to a desired diameter. The thin wall of the sheath is fabricated from a rectangular piece of material such as metal or plastic with two cut edges. The rectangular piece of metal or plastic is rolled tightly to create the small diameter configuration that is inserted into the patient. A cam or control member is affixed to the innermost edge of the rectangular piece of metal or plastic. The control member extends to the proximal most portion of the sheath. By rotating the control member, the operator causes the thin wall piece of rolled material to unfurl into a larger or smaller diameter, depending on the direction of rotation. A mechanical lock at the distal end of the sheath permits the control member to be selectively constrained from rotation and thus lock the sheath diameter in place.

11 Claims, 10 Drawing Sheets

U.S. PATENT DOCUMENTS

| | | |
|---|---|---|
| 5,176,659 A | 1/1993 | Mancini |
| 5,201,756 A | 4/1993 | Horzewski et al. |
| 5,306,294 A * | 4/1994 | Winston et al. ............ 623/1.11 |
| 5,318,588 A * | 6/1994 | Horzewski et al. .......... 606/198 |
| 5,320,611 A | 6/1994 | Bonutti et al. |
| 5,569,218 A * | 10/1996 | Berg ......................... 604/525 |
| 5,573,517 A | 11/1996 | Bonutti et al. |
| 5,674,240 A | 10/1997 | Bonutti et al. |
| 5,846,251 A | 12/1998 | Hart |
| 5,873,817 A * | 2/1999 | Kokish et al. ............... 600/143 |
| 5,888,196 A * | 3/1999 | Bonutti ..................... 600/204 |
| 5,971,938 A | 10/1999 | Hart et al. |
| 5,997,508 A | 12/1999 | Lunn et al. |
| 6,090,072 A | 7/2000 | Kratoska et al. |
| 6,183,443 B1 | 2/2001 | Kratoska et al. |
| 6,187,000 B1 | 2/2001 | Davison et al. |
| 6,210,370 B1 | 4/2001 | Chi-Sing et al. |
| 6,293,909 B1 | 9/2001 | Chu et al. |
| 6,312,443 B1 | 11/2001 | Stone |
| 6,471,684 B2 * | 10/2002 | Dulak et al. ................ 604/523 |
| 6,524,320 B2 | 2/2003 | DiPoto |
| 6,616,678 B2 * | 9/2003 | Nishtala et al. ............. 606/198 |
| 6,652,553 B2 | 11/2003 | Davison et al. |
| 6,679,902 B1 | 1/2004 | Boyle et al. |
| 2002/0169495 A1 | 11/2002 | Gifford et al. |
| 2003/0065353 A1 | 4/2003 | Horzewski et al. |
| 2003/0195549 A1 | 10/2003 | Davison et al. |
| 2003/0195551 A1 | 10/2003 | Davison et al. |
| 2003/0216770 A1 | 11/2003 | Persidsky et al. |
| 2004/0006344 A1 | 1/2004 | Nguyen et al. |
| 2004/0087968 A1 | 5/2004 | Core |

* cited by examiner

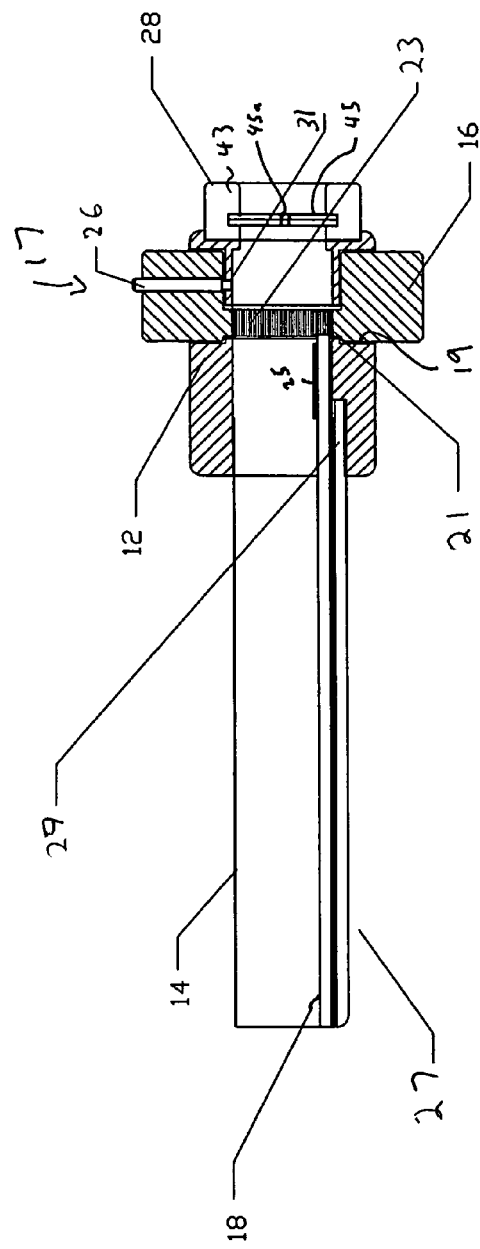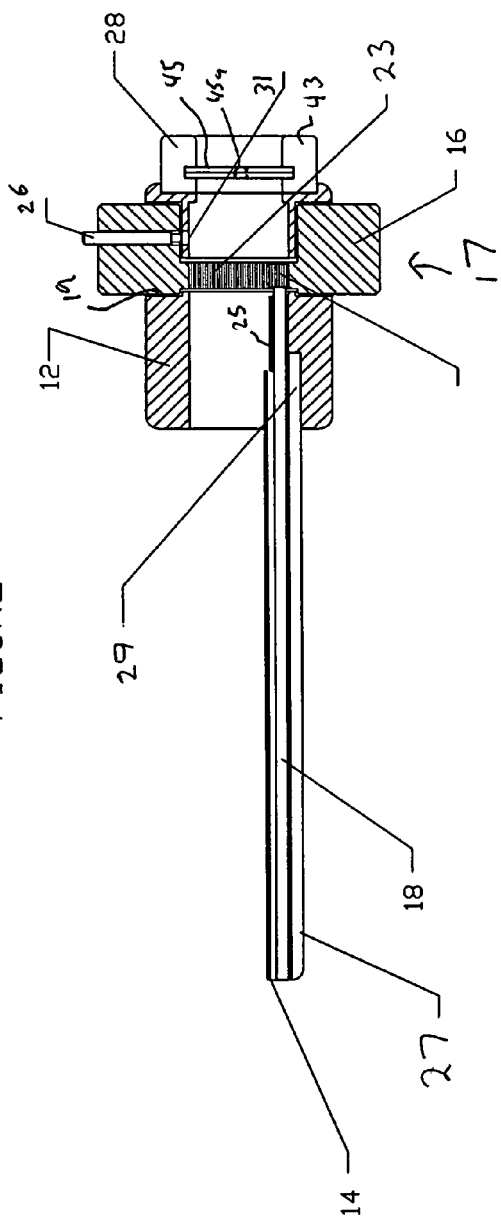

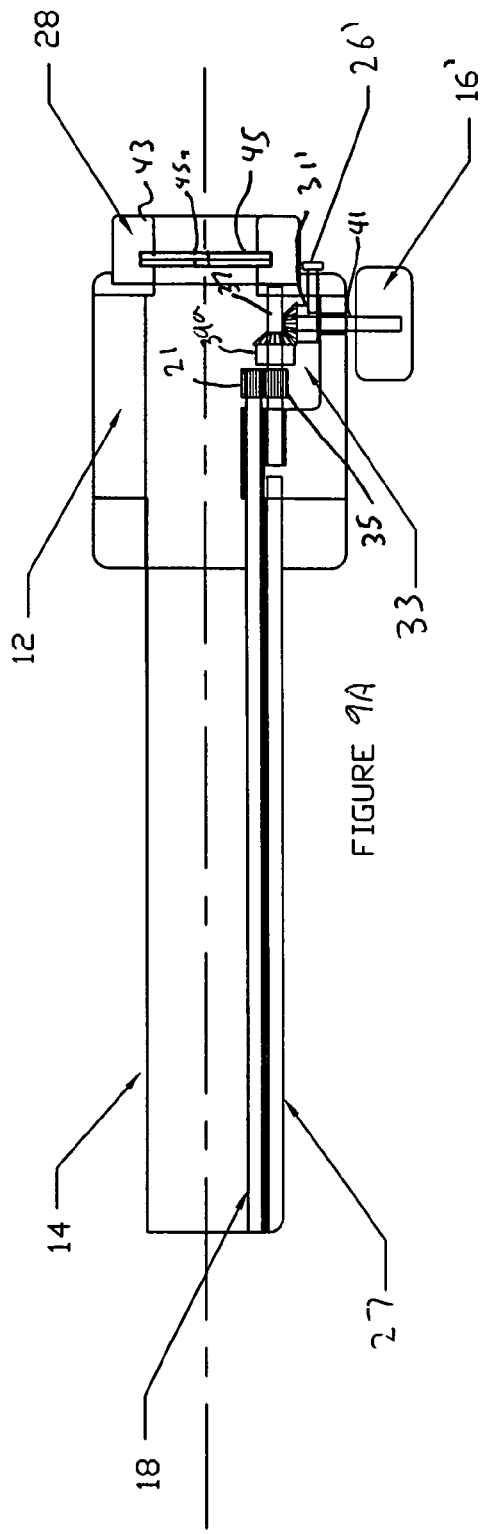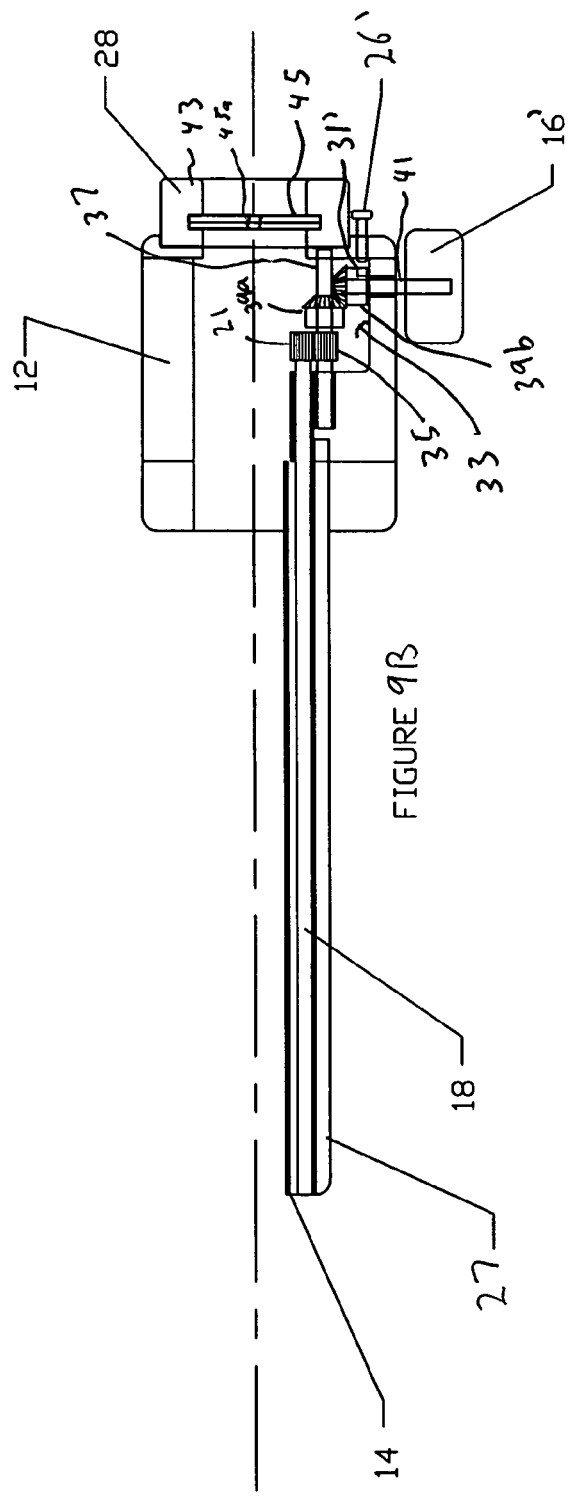
FIGURE 9A
FIGURE 9B

EXPANDABLE MEDICAL ACCESS DEVICE

This application claims the priority benefit under 35 U.S.C. § 119(e) of Provisional Application 60/554,338 filed Mar. 18, 2004.

BACKGROUND OF THE INVENTION

1. Field of the Invention

This invention relates to medical access devices and, in particular, to expandable medical access devices for providing minimally invasive surgical access for various surgical procedures.

2. Description of the Related Art

A wide variety of diagnostic or therapeutic procedures involve the introduction of a device through a natural or artificially created access pathway. As such, minimally invasive access systems have been developed to generate such pathways. A general objective of these access systems is to minimize the cross-sectional area of the puncture, while maximizing the available space for the diagnostic or therapeutic instrument. Procedures that utilize access systems include, among others, a wide variety of laprascopic diagnostic and therapeutic interventional procedures.

In many of these procedures, it is advantageous to provide a self-retaining access system that provides tissue retraction throughout a surgical procedure without the continued attention of a human assistant. Self-retaining retraction provides the operator with the ability to choose the tissue and separation plane to provide adequate exposure for a given surgical procedure. Examples of tissues retractors commonly known in the surgical art include the Richardson retractor, the Alm retractor, the Balfour retractor, the Rigby retractor and the like.

In contrast to minimally invasive access systems, surgical approaches, by their open nature, generally require the elements of incision, dissection, hemostasis, and mechanical closure. The incision is typically accomplished using a scalpel, a saw, or an electrosurgical cutting device. Dissection is typically accomplished using a scalpel, electrosurgical cutting device, or a blunt object such as a pair of forceps or an obturator. Hemostasis control is generally performed using electrocautery, wound packing, and suction drainage to a collection system. Mechanical closure is generally accomplished using sutures, staples or clips.

Surgical approaches afford direct surgical vision, direct tactile feedback along with the intrinsic ability to enlarge the field of view simply by enlarging the incision and resetting the self retaining retractor. While large incisions may heal as quickly as small ones, they are a source of extended patient discomfort and poor cosmetics along with expensive recovery periods, both in and out of the hospital.

Many surgical procedures have been converted to minimally invasive, laparoscopic procedures that avoid large incisions, reduce hospital stays and costs while producing similar short- and long-term results. Such procedures typically involve minimally invasive access systems as described above. However, minimally invasive access systems for surgical procedures that do not invade body cavities, such as the abdomen or thorax may not be suited for traditional laparoscopic visualization. Such is the case in orthopedic procedures (e.g., joint or spine access). In these cases, a surgeon often is forced to rely on the blunt placement of consecutively larger cannula, with or without the benefit of a dilator to reach the desired surgical site. Surgical instruments are then inserted through the cannula to reach the target site. Surgical exposure is limited by the accurate placement of the cannula, location of pathology and diameter of the cannula. Once the skin incision of adequate size is made, the axial shear force of sequentially placed dilators, with increasing diameters, creates an operative tunnel to reach the desired surgical site.

The rigid walls of the cannula exert a tamponade pressure to provide hemostasis during the session. Distal visualization is often provided by a rigid scope while operative maneuvers are accomplished with laparoscopic or extended length instruments placed through the cannula. Radial pressure holds the cannula over the operative site freeing the operative team from retraction duties as well as removing potential obstructive nuisances from the immediate surgical field. Enlarging the surgical field requires placement of a larger cannula with an axially directed shear force. Such placement of a new cannula carries with it the possibility of loosing anatomic landmarks during the device transition. Since a majority of the tissue plane separation is achieved with blunt expansive force, rather than by tissue shearing, and is maintained with radial force, recovery is often less traumatic than that encountered with open surgery. Should the operative procedure require expansion with incision and traditional retraction applied, the recovery course may be longer and costs higher than if the minimally invasive approach was used.

Traditional laparoscopy also uses trocars, with diameters ranging from 5 to 20 mm, to gain access to the abdomen or chest. Most procedures are successfully completed through three or four trocar sites. There are cases, such as removing an organ or tissue for transplant, when time and labor burden could be reduced by the ability to enlarge a trocar site. Surgical incision sites must enlarged carefully, however, because most operators are reluctant to expand surgical exposure at the risk of losing the anatomic landmark.

A need therefore remains for improved access technology needed to create a tunnel to a target surgical site in such a way that trauma to the tissue is minimized. Preferably, such technology provides for controllable tissue dilation once the initial tunnel is created.

SUMMARY OF THE INVENTION

Accordingly, one embodiment of the present invention relates to an access apparatus for providing minimally invasive surgical access that comprises a tubular member formed from a rolled sheet of thin walled material. The thin walled material includes an inner surface, an outer surface, an inner edge and an outer edge. A first component is coupled an inner portion of the thin walled material and a second component coupled to an outer portion of the thin walled material. An actuation mechanism is configured such that rotation of the first component with respect to the second component unwinds the rolled sheet of thin walled material to increase the diameter of the tubular member.

Another embodiment relates to a method for providing minimally invasive surgical access. The method comprises inserting a wound thin walled sheath into an animal or patient through a small surgically created incision. The sheath is advanced to the target surgical site. The sheath is selectively, and controllably unwound such that the sheath expand to a desired diameter.

In another embodiment of the present invention, an access apparatus comprises a sheath that is fabricated from a thin walled sheet of material. The piece of material is rolled tightly to create a small diameter configuration that is inserted into the patient. A control member is coupled to the sheath near an innermost edge of the sheath. The control member extends substantially to the proximal most portion of the sheath. By rotating the control member, the operator causes the thin wall sheet of metal or plastic to unfurl into a larger or smaller diameter, depending on the direction of rotation. A mechanical lock at the proximal end of the sheath permits the control member to be selectively constrained to prevent rotation and thus lock the sheath diameter in place. In a modified embodiment, the sheath may be supplied with an internal obturator, a proximal seal for instruments, and/or insulation to prevent or minimize the escape of energy, fluids, or contaminants from the interior of the sheath to surrounding tissue.

In yet another embodiment, a laparoscopic version of the sheath is used to create a dome over the surgical site. The dome is created at the distal end of the sheath and is preferably radially dilated separately from the sheath. The dome is, in this embodiment, a separate winding of material with a separate control member that passes through or alongside the sheath. An elastomeric, expandable, or unfurling material connecting the delivery sheath to the dome provides a seal at the proximal end of the dome to isolate tissues captured within the dome from surrounding tissues. The exterior of the device would gently move uninvolved organs and tissue out of the surgeon's area of interest. The interior of the dome would provide adequate space for visualization, sewing and clipping for hemostasis as well as for tissue re-approximation. Infusion and removal of fluids are preferably available to maintain a clear surgical field.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

FIG. 8A is a partial cross-sectional view of the access sheath of FIG. 2A;

FIG. 8B is a partial cross-sectional view of the access sheath of FIG. 1A;

FIG. 9A is a partial cross-sectional view of a modified embodiment of an access sheath in an expanded configuration;

FIG. 9B is a partial cross-sectional view of the access sheath of FIG. 9A in a collapsed configuration;

DETAILED DESCRIPTION OF THE PREFERRED EMBODIMENTS

Figure 10A:
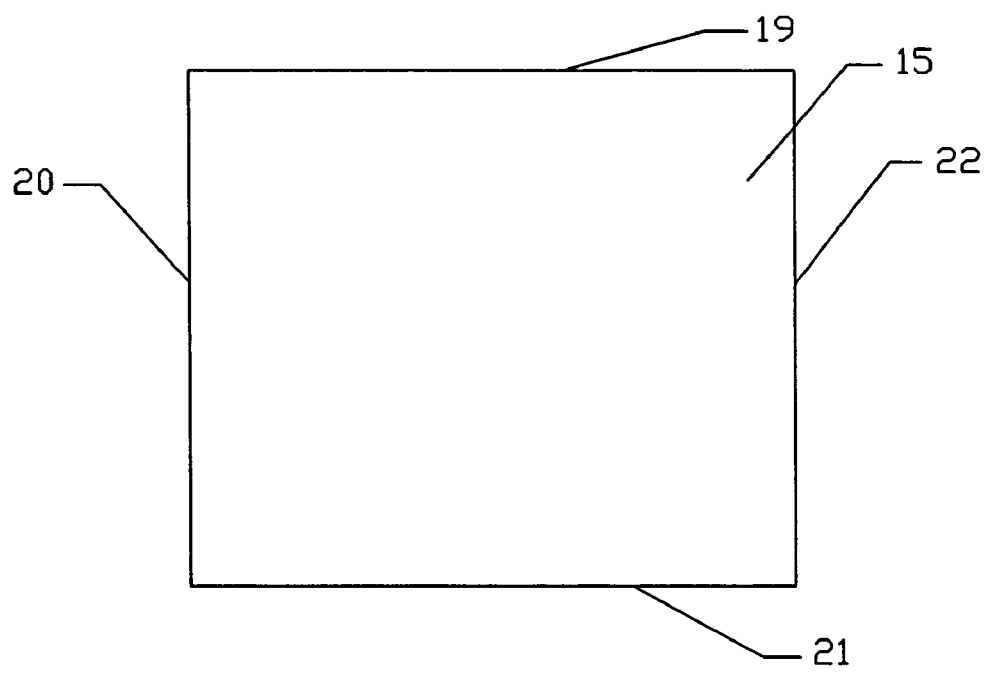
FIG. 10A is a top view of a thin walled material, which forms a part of the access sheath of FIG. 1A.
Figure 10B:
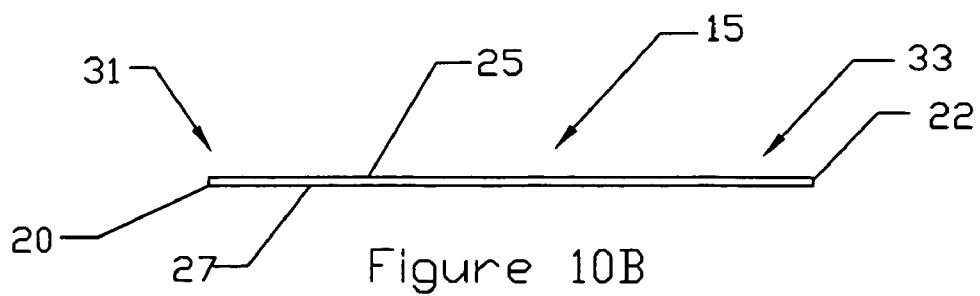
FIG. 10B is a side view of the thin walled material of FIG. 10A.

FIG. 1A illustrates a side perspective view of an exemplary embodiment of an access system 10 in its radially compressed configuration. FIG. 2A is a side perspective view of the access system 10 of FIG. 1A in an expanded or enlarged profile configuration. The system 10 comprises a proximal hub 12 and a tubular shaped sheath 14, which is formed from a thin walled material 15 that is wound about its longitudinal axis. With reference to FIGS. 10A and 10B, in the illustrated embodiment, the thin walled material comprises a generally longitudinally oriented outer edge 20, a longitudinally oriented inner edge 22, a proximal edge 19, a distal edge 21, a periphery surface 25 and a lumen facing surface 27. When wound about its longitudinal axis, the thin walled material 15 defines a central lumen 30 (see FIGS. 1A and 2A). In the illustrated embodiment, the hub 12 comprises a tubular member 23, which forms an inner lumen 24.

In the compressed configuration (FIG. 1A), the sheath 14 has a reduced cross-sectional profile. As mentioned above, the sheath 14 is formed by winding the thin walled material around its longitudinal axis to form overlapping layers of the thin walled material 15. In the expanded configuration (FIG. 2A), the sheath 14 has an enlarged cross-sectional profile that is formed as the overlapping layers of the thin walled material are unwound. In the enlarged configuration, the tubular shaped sheath 14 is formed from less overlapping layers of the thin walled material 15 as compared to the compressed configuration.

As will be explained in detail below, the access system 10 is preferably configured such that the sheath 14 may be controllably expanded from the compressed configuration to the enlarged configuration. That is, the sheath 14 may be selectively expanded to at least one cross-sectional profile between the compressed configuration and the enlarged configuration. In this manner, the access system 10 allows the surgeon to selectively enlarge the access site. As such, the access system preferably includes an actuator mechanism 7 for controlling the expansion of the sheath 14.

In the illustrated embodiment, the sheath 14 is selectively expanded by coupling an inner portion 33 of the thin walled material 15 to a first component and coupling an outer portion 31 of the thin walled material 15 to a second component. By rotating the first component relative to the to the second component, the outer and inner portions 31, 33 of the thin walled material 15 are rotated relative to each other. In this manner, the thin walled material 15 may be wound or unwound to decrease or increase the diameter of the tubular sheath 14. The outer and inner portions 31, 33 of the thin walled material 15 refer to the portions of the thin walled material at or functionally near the outer edges 20, 22 respectively. In some embodiments, the outer an inner portions 31, 33 may include portions of the thin material 15 that are distanced from the outer and/or inner edges 20, 22 but preferably such distance is not great enough to interfere with the winding or unwinding of the tubular sheath 14. In a similar manner, the first component may be attached to the lumen facing surface 27 of the thin walled material 15 while the outer component may be coupled to the peripheral surface 25 of the thin walled material 15.

With reference now to the illustrated embodiment of FIGS. 1A and 2A, the first component comprises a cam or torque member 18, which is coupled to a winding knob 16. The second component comprises the tubular hub 12. The winding knob 16 further comprises a lock 26 and a seal 28 as described below.

The user may use the hub 12 for griping for the system 10 as a point of stability. With reference to FIGS. 8A and 8B, the winding knob 16 of the illustrated embodiment comprises a generally tubular body 17 that is positioned within a recess 19 of the hub 12 such that the knob 16 may rotate in the circumferential direction about its longitudinal axis but longitudinal movement between the knob 16 and the hub 12 is constrained.

With continued reference to FIGS. 8A and 8B, in the illustrated embodiment, the proximal end of the torque member 18 comprises a gear 21 and is journalled for rotation within a journal 25 supported by the hub 16. The gear 21 engages a winding gear 23 formed on the internal bore of the winding knob 16. In this manner, as the winding knob 16 is rotated the torque member 18 is rotated. At least a portion of the torque member 18 and preferably at least some central region and/or the distal of the torque member 18 is coupled to the inner portion 33 of the sheath 14 preferably on the lumen facing side 27. The hub 12, in turn, is preferably coupled to the proximal end of the outer portion 31 of the sheath 14 preferably on the peripheral side 25. As shown in FIG. 8A, in the illustrated embodiment, the hub 12 is coupled to the sheath 14 through a static rod 27, which may be coupled to the outer portion 31 of the sheath and to the hub 12 at its proximal end 29 so that it does not rotate. In a modified embodiment, the outer portion 31 could be coupled to torque member 18 while the inner portion 33 is coupled to the hub 12 directly or through a static rod 27 or other intermediate member. In such an embodiment, excess material would be wound onto the torque member. It should be noted, that FIGS. 1A-2A illustrate a modified embodiment that does not include the static rod 27.

The actuating mechanism 17 is preferably configured to limit the rotation of the first component with respect to the second component. In the illustrated embodiment, the actuating mechanism 17 includes the lock 26, which is configured to constrain the rotation of the knob 16 with respect to the hub 12. For example, a positive lock that is engaged to prevent, or disengaged to allow, relative rotation between the winding knob 16 and the hub 12 may be used. In the illustrated embodiment, the lock 26 comprises a peg or radially oriented projection that selectively engages holes 31 or indents in the hub 12, thus providing a locking feature. In another embodiment, the lock 26 is a ratcheting type mechanism that permits rotation of the winding knob 16 with binding or frictional click-stops. In such an embodiment, the proximal locking or ratchet mechanism 26 holds or maintains the diameter selected by the surgeon. Those of skill in the art will also recognize other configurations for the lock 26 given the description herein. The proximal lock assembly 26 is preferably of small mass and profile to avoid interfering with surgical maneuvers. The lock 26 is preferably configured not require the attention of an assistant to maintain position or size. The hub 12 may also include various wings, extensions, hooks, straps etc. may be selectively coupled to the hub placed at skin level and selectively affixed to the hub 12 to assist with stabilization.

It is anticipated that various other types of actuating mechanisms may be used to rotate the torque rod 18 in light of the disclosure herein. For example, FIGS. 9A and 9B illustrate an embodiment in which the hub includes a gear box 33. The gear box 33 includes a winding gear 35 for engaging the gear 21 on the end of the torque rod 18. The winding gear 35 is positioned on a shaft 37 journalled for rotation in the hub 12. A bevel gears 39a is coupled to the shaft 37 and is rotated by a second bevel gear 39b. The second bevel gear 39a, in turn, is coupled to a shaft 41, which extends outside the hub 12 and is attached to a winding knob 16'. In this manner, as the winding knob 16' is rotated about an axis generally perpendicular to the longitudinal axis of the device 10, its rotation is converted to rotation of the toque road 18 about an axis generally parallel with the longitudinal axis of the device 10. In this embodiment, the lock comprises a pin or peg 26' that extends through the hub 12 to selectively engage a hole 31' on the second bevel gear 39b.

In another modified embodiment of the system 10, the actuating mechanism 17 may be configured for one-handed operation. In one such embodiment, the actuating mechanism 17 may comprise a lever or button that is depressed by squeezing the hand around the hub 12 and the winding knob 16. By squeezing the hand, the lever may rotate the winding knob 16 such that and the torque member 18 rotates either clockwise or counterclockwise. The lever may be spring biased to expand outward fully after being forced into the hub 12 and then released. A ratchet mechanism (not shown) permits outward movement of the lever without rotating the torque member 18. Accordingly, repeated compression of the lever provides additional rotation of winding knob and the torque member 18 and corresponding expansion or contraction of the diameter of the working length of the sheath 10. A reverse switch or lever may be provided for reversing the direction of the rotation of the torque member given continued compressions of the winding knob 16 toward the hub 12. Other forms of one-handed operation are useable for this application including those using motor drives and a power source such as electricity, pneumatics, or hydraulics. With the one-handed embodiment, it is possible for the user to rotate the torque member 18 with the same hand used to hold the hub 12 of the sheath 10.

In the configurations described above, the actuating mechanism 17 preferably allows the sheath 14 to be selectively expanded to at least one cross-sectional profile and preferably a plurality of discrete intermediate cross-sectional profiles throughout a continuum between the largest and the smallest diameter and maintained at that size because of the lock 26. The hub 12 and/or the knob 16 preferably include visual indicia 31 (e.g., notches, lines, numbers, graduations etc) that indicate either the diameter inside or outside of the tubular sheath 14 for a specific positions of the actuating mechanism 17.

With reference back to FIGS. 8A and 8B, the seal 28 is affixed to the proximal end of the winding knob 16 and either rotates with the winding knob 16 or is configured to remain rotationally stationary relative to the winding knob 16. In the illustrated embodiment, the seal 28 is affixed so as to be axially stationary relative to the winding knob 16 and comprises a housing 43 that may be fabricated from the same materials as those used to fabricate the hub 12. The seal 28 further comprises an elastomeric membrane 45 that is suspended within the seal housing 43. The elastomeric membrane 45 is generally configured as a washer with a central orifice 45*a* capable of accepting instruments therethrough and sealing to the outer surface of said instruments. The central orifice 45*a* of the elastomeric membrane 45 enlarges or shrinks as necessary to accommodate a wide range of instruments. The orifice diameter of the elastomeric membrane 45, in the unstretched state may range from 0.1 inches to 1 inch. The elastomeric membrane 45 may be fabricated from materials such as, but not limited to, silicone elastomer, thermoplastic elastomer, polyurethane, latex rubber, and the like. The elastomeric membrane 45 is preferably coated with a lubricant such as silicone oil or PTFE to minimize friction on passage of an instrument. The seal 28 is, in a preferred embodiment, capable of providing hemostasis against blood loss at systemic arterial pressures of 100 mm Hg or more.

With reference to FIG. 1A, the tubular sheath 14 may be fabricated from materials such as, but not limited to Elgiloy, nitinol, titanium, polytetrafluoroethylene (PTFE), stainless steel, polyimide, polyester, and the like. The tubular sheath 14 may be coated with materials such as, but not limited to, PTFE, fluoroethylene polymer (FEP), paralene, silicone oil or the like, to minimize friction when the tubular sheath 14 diameter is changed because the layers of the material 15 may slide relative to each other. The tubular sheath 14 may further be coated on one or both sides with antithrombogenic agents such as, but not limited to heparin, which is ionically or covalently bonded to the tubular sheath 14. The tubular sheath 14 may also be coated with antimicrobial agents such as, but not limited to, silver oxide, silver azide, betadine, or the like. The tubular sheath 14 may further be configured to carry electrical charge so that it can be used as the electrode for microwave or radio frequency (RF) energy which can be used to cauterize or destroy cellular tissue.

In certain embodiments, the wall thickness of the thinned walled material 15 ranges from about 0.0002 inches to about 0.010 inches and is often between about 0.0005 and about 0.005 inches. The tubular sheath 14 is preferably dimensioned such that at least one 360-degree wrap is obtained in the fully expanded or dilated configuration. The tubular sheath 14 is more preferably such that at least two wraps, encompassing 720 degrees (i.e., 360 degrees of overlap) are obtained from the tubular sheath 14 in the fully expanded or radially dilated configuration.

The working length of the tubular sheath 14 is determined generally by the distance between the skin surface and the target surgical site. The tubular sheath 14 may have a working length from about 1 cm to about 150 cm and is often between about 5 cm and about 30 cm. The working length is that distance between the distal most edge of the tubular sheath 14 and the distal end of the hub 12. The radial strength of the tubular sheath 14 is preferably configured such that it is sufficient to expand most soft tissue in a uniform circular fashion. Those of skill in the art will recognize that the desired radial strength may be achieved by selecting the combination of the strength and thickness of the material and the number of multiple layers of the thin walled material 15 to create a structure that has sufficient resistance to hoop stress and point loads. In one embodiment, the distal edge of the tubular sheath 14 is sharp in that the material of the tube is not edge treated in any way. The distal edge of the tubular sheath 14 is, in another embodiment, atraumatic and not substantially sharp. In this embodiment, the distal edge of the thin tubular sheath 14 is rendered blunt and atraumatic by bending, folding, rolling, coating with a polymer, or other technique known in the medical art. Appropriate strain relief is added to the material of the distal edge of the tubular sheath 14 in the atraumatic folded, bent, or rolled configuration.

It will be apparent from the disclosure herein that the access sheath 14 and/or the methods described herein may also find utility in a wide variety of diagnostic or therapeutic procedures that require an artificially created access tract. For such applications, the diameter of the tubular sheath 14 in the radially collapsed configuration and its expanded or enlarged configuration will depend upon the intended surgical application. For example, depending upon the application, the collapsed diameter of the sheath 14 may lie in the range from about 1 mm to about 10 millimeters. The expanded diameter of the sheath 14 may lie in the range from about 4 mm to about 50 mm. The wide variety of diagnostic or therapeutic procedures may include but are not limited to many urological applications (e.g., the removal of ureteral strictures and stones, the delivery of drugs, RF devices and radiation for cancer treatment, etc.), gastrointestinal applications (e.g., to the removal gallstones and appendix procedures, colon therapies, esophageal treatment and the treatment of bowel obstructions), cardiovascular applications (e.g., to provide access for minimally invasive heart bypass, valve replacement or the delivery of drugs or angiogenesis agents), vascular applications (e.g., minimally invasive access to the aorta or contralateral leg arteries for the treatment of, for example, an abdominal aortic aneurysm), gynecological applications (e.g., endometrial therapies, delivery of drugs, delivery of cancer agents, sterilization procedures, etc.), orthopedic applications and breast biopsies/lumpectomies.

The hub 12, the winding knob 16, and the lock 26 are preferably fabricated from materials such as, but not limited to, Acrilonitrile Butadiene Styrene (ABS), polyvinyl chloride (PVC), polyethylene, polypropylene, and the like. As shown in FIG. 1A, the winding knob 16 is affixed coaxial with the hub 12. In another embodiment, the winding knob 16 comprises removable key or lever fitted into the proximal portion of the torque member 18 to operate (deploy and retract) the thin wall wound tube 14 in response to surgical considerations as determined by the surgeon. In this embodiment, the winding knob 16 may or may not be aligned along with or coaxially to the axis of the hub 12. Gearing or other mechanisms may be used to transmit the rotational energy to a winding knob 16 that is oriented with its axis lateral to the axis of the hub 12.

The torque member 18 is preferably fabricated from materials such as, but not limited to, polyester, polyamide, stainless steel, Elgiloy, nitinol, and the like. The torque member 18 is preferably sized so that its length is slightly longer than that of the thin wall wound tube 14. The diameter of the torque member 18 is preferably between 0.020 inches and 0.4 inches and more preferably between 0.30 inches and 0.25 inches.

In an embodiment of the system 10, the tubular sheath 14 is sheathed with an elastomeric seal layer fabricated from materials such as, but not limited to, silicone elastomer, C-Flex thermoplastic elastomer, polyurethane, or the like. The elastomeric seal layer fully encloses and seals the tubular sheath 14 which otherwise has a spiral channel of communication between the inner lumen and the exterior aspect of the tube 14. The elastomeric seal layer may be disposed either on the inner diameter or the outer diameter of the tubular sheath 14. In another embodiment, the seal layer is substantially inelastic but is folded in the radially compressed configuration and unfolded in the radially expanded configuration. Such unfurling seal layer is similar in structure to an angioplasty balloon and is affixed either to the inner diameter or outer diameter of the thin wall wound tube 14. The unfurling seal layer is affixed to the tubular sheath 14 so that circumferential relative motion is permitted, since the tubular sheath 14 winds and unwinds and the unfurling seal layer furls and unfurls. The unfurling seal layer is fabricated from materials such as, but not limited to, PTFE, polyurethane, polyethylene, polypropylene, polyamide, polyester, and the like. The wall thickness of the unfurling seal layer may range from 0.0002 to 0.010 inches and is preferably between 0.0005 and 0.005 inches.

FIGS. 1B and 2B illustrate an enlarged view of the distal end of the sheath system 10 in the compressed and enlarged configurations. The spiral nature of the thin wall wound tube 14 is more clearly visible in this illustration as is the distal end of the cam or torque member 18. Note that the number of layers in the wall of the sheath 10 is reduced as the diameter of the through lumen 30 is increased.

In one embodiment of the method of use, the surgeon forms an incision in the patient's skin and continues the incision to a target depth. The incision may be created using a cutdown or a percutaneous method such as that known as the Seldinger technique. The tubular sheath 14 may be inserted into the incision and advanced until the distal end reaches a target depth.

With the distal end in place, the sheath is controllably expanded. In one embodiment, this involves rotating the torque member 18 with respect to the outer portion 31 of the thin walled material 15. With the sheath expanded, the lumen forms a working lumen through used in a wide variety of diagnostic or therapeutic procedures. If, during the procedure, a larger working lumen is required, the tubular sheath 14 may be further expanded by additional rotation of the torque member 18 with respect to the outer portion of the thin walled material 15. When the procedure is completed, the rotation of the torque member 18 with respect to the outer portion 31 may be reversed to reduce the cross-sectional profile of the tubular sheath 14. With the cross-sectional profile reversed, the access system 10 may be withdrawn from the incision.

In a further embodiment, the sheath includes a guidewire channel, either through the central lumen 30 of the radially collapsed system 10 itself or through the center of a removable obturator. This guidewire channel provides the ability to insert the sheath, in its small diameter configuration, over a guidewire.

As mentioned above, the access system 10 may be used in a wide variety of diagnostic or therapeutic procedures. For example, in a further embodiment, the access system may comprise an insulating barrier placed on the outside, or inside, of the tubular sheath 14 to confine therapeutic or diagnostic cryogenic temperatures, radio frequency (RF) waves or microwaves so that they would not reach tissues surrounding the sheath. Instead of sustaining losses along the length of the sheath, these energies are focused substantially on the tissue or organ targeted by the device at or near its distal end. In another embodiment, a seal layer is provided that prevents migration of fluids and other materials through the wall of the sheath. An insulating exterior or interior barrier that protects displaced, healthy tissue from destructive treatments being applied to diseased tissue within the confines of the device. Electrical, thermal and radiated options should be incorporated. Tissue treated in this manner could be desiccated and rendered inert and of a reduced size for more easy removal. Furthermore, healthy tissue outside the sheath is protected against contamination by pathological tissue being removed or accessed by the sheath. Such protection of healthy tissue is especially important in the case of malignant or carcinogenic tissue being removed through the sheath so that potential spread of the disease is minimized. For the purposes of endovascular use, the sheath insulating barrier may be used to prevent blood loss through the walls of the sheath, thus providing for hemostasis.

In another embodiment, the sheath may be used as a probe under radiographic guidance (fluoroscopy, computer aided tomography (CAT), magnetic resonance imaging (MRI), or ultrasound). The sheath may further be inserted and manipulated under direct vision by including a small caliber scope to identify an anatomic path or features within a body cavity.

In another embodiment, the system is configured such that the sheath 14 is deploy at the distal portion of a long concentric control cam. The inner member may be held stable while the outer member deploys or compresses the distal device to contain an organ or create an operative tunnel to gain surgical access to distant anatomic structures while displacing other healthy (or pathological) tissue under visual control.

In another embodiment, the device can be introduced via standard laparoscopic trocar and be selectively expanded to stabilize an organ or tissue with known, controlled circumvention pressure to provide the operator with a stable operative surface. Additionally, the device can be positioned to displace organs and structures to create a stable tunnel to expose a distant operative site.

Another embodiment comprises a method of use wherein the device is inserted as part of a system to capture an organ. The sheath is inserted to allow safe withdrawal of another device designed to contain the amputated organ or tissue, which can then be withdrawn through the sheath to a position outside that of skin level. This method conveys the benefit of laparoscopic surgery while avoiding the challenges associated with isolated removal of a diseased organ where malignant cell isolation is of a concern.

In accordance with an embodiment of use, a diseased organ or tissue mass is isolated by the surgeon by inserting the sheath to the target mass. An instrument can then be inserted through the sheath. These instruments may allow for various methods of cell or tissue destruction to be employed, with or without specimen removal. Access to the diseased organ may be accomplished under direct vision as part of a laparoscopic or percutaneous procedure. Exemplary uses of a sheath that may be selectively enlarged include applications in procedures to remove kidney stones, perform biopsies or organ removal, perform implantation of spinal devices or devices to repair damaged orthopedic joints, and the like. The sheath is capable of being made smaller or larger in diameter to accommodate the size changes that are often required and sometimes unanticipated in a procedure. Following completion of the procedure, the sheath is removed from the patient, with or without the step of reducing the size of the sheath before removal.

In one embodiment of use, once an initial tissue target is identified and the appropriate location of the access confirmed, an access device can, under direct, precise operator control, enlarge the access lumen by applying radial force. The surrounding tissue applies a counter pressure to that exerted by the radially dilated device, which aids in maintaining stability of the device once it is expanded. The overall diameter of the sheath can be reduced, at operator discretion, by rotating a winding knob, dilating knob, or other control affixed to the torque member that extends axially along one edge of the sheath thin wall material.

Figure 1:
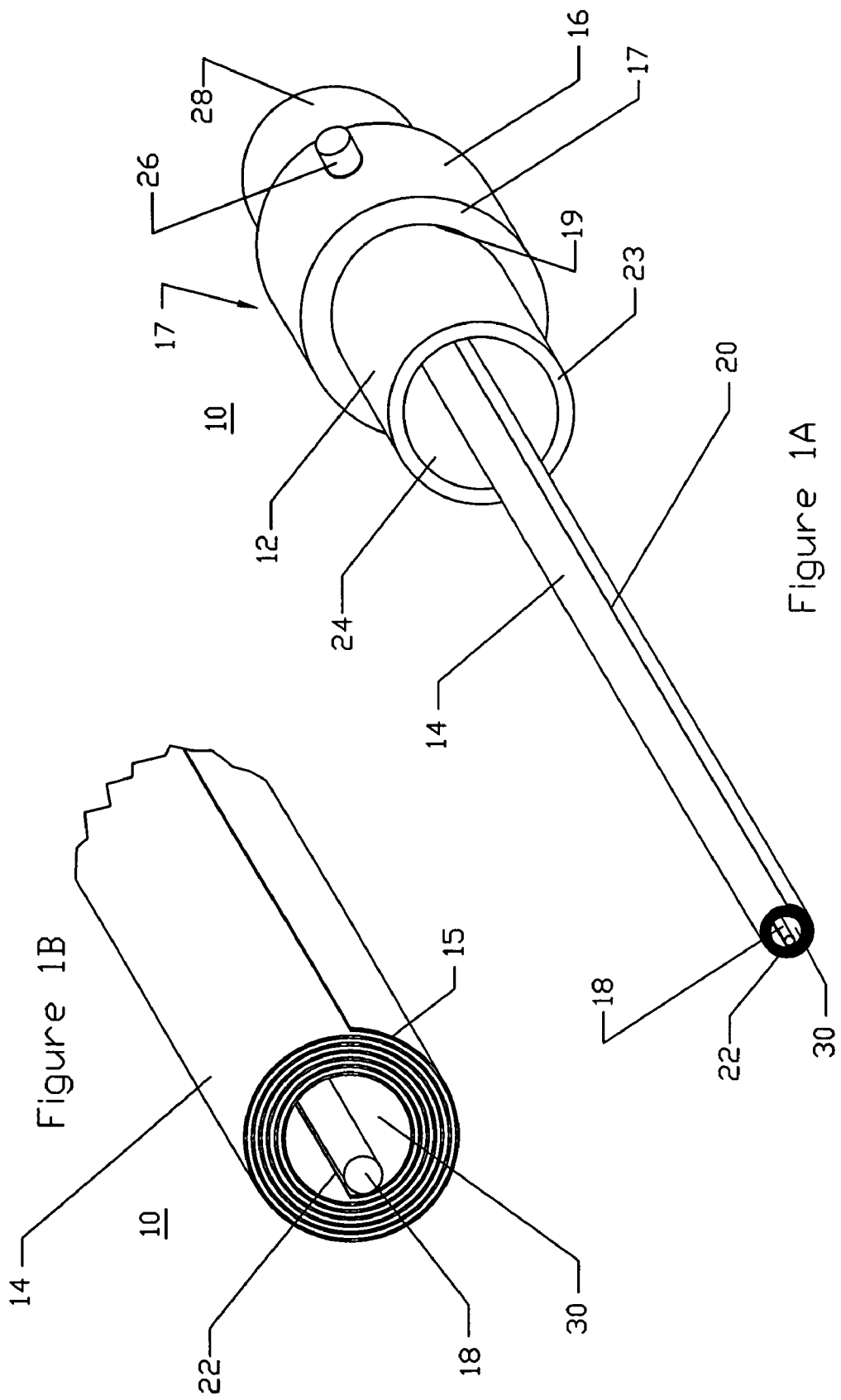
FIG. 1A is a side perspective view of an exemplary embodiment of an access sheath in a compressed or reduced profile configuration.
FIG. 1B is a closer view of a distal end of the access sheath of FIG. 1A.
Figure 2:
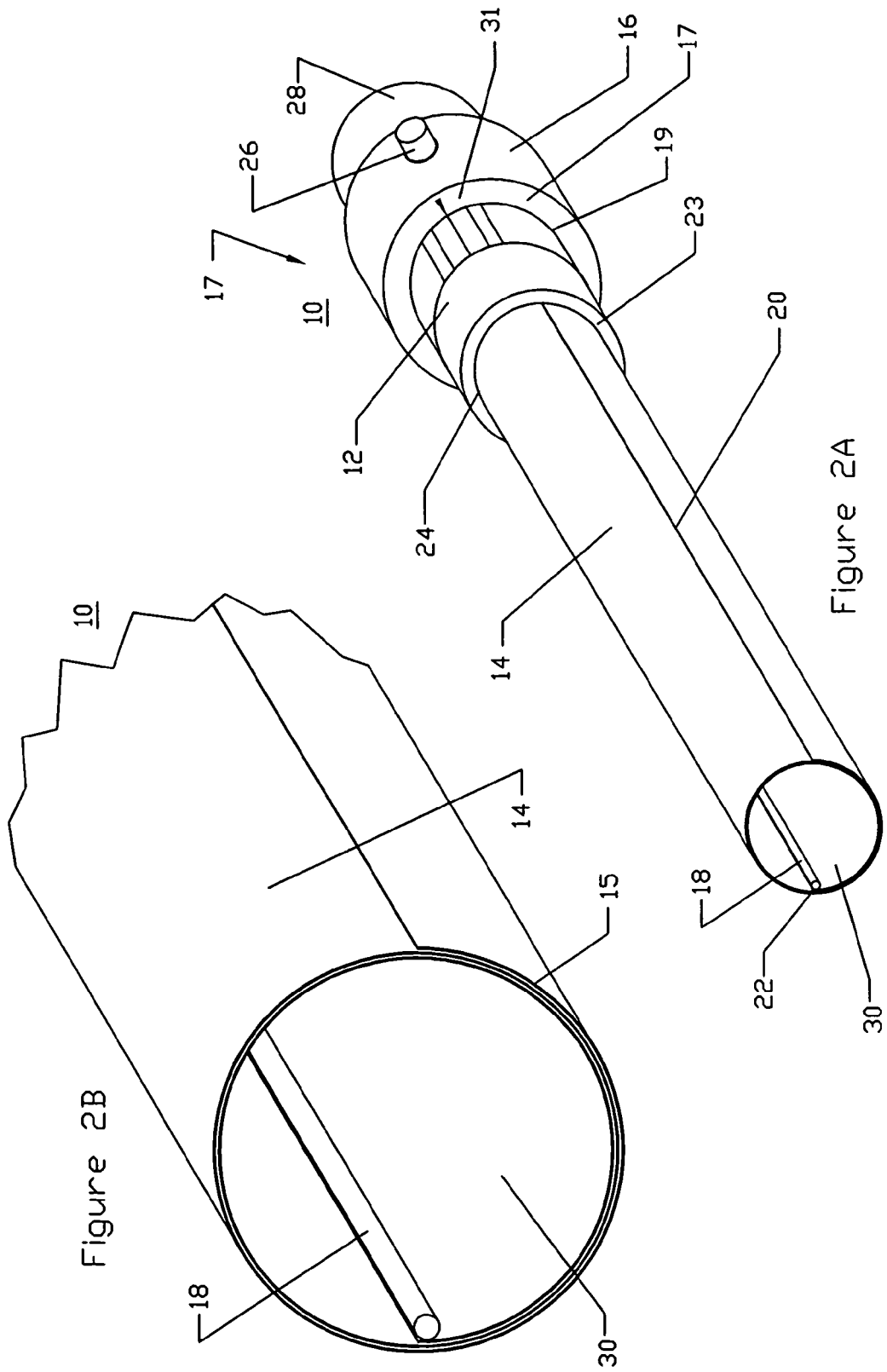
FIG. 2A is a side perspective view of the sheath of FIG. 1A in an expanded or enlarged profile configuration.
FIG. 2B is a closer view the distal end of the sheath of FIG. 2A.
Figure 3:
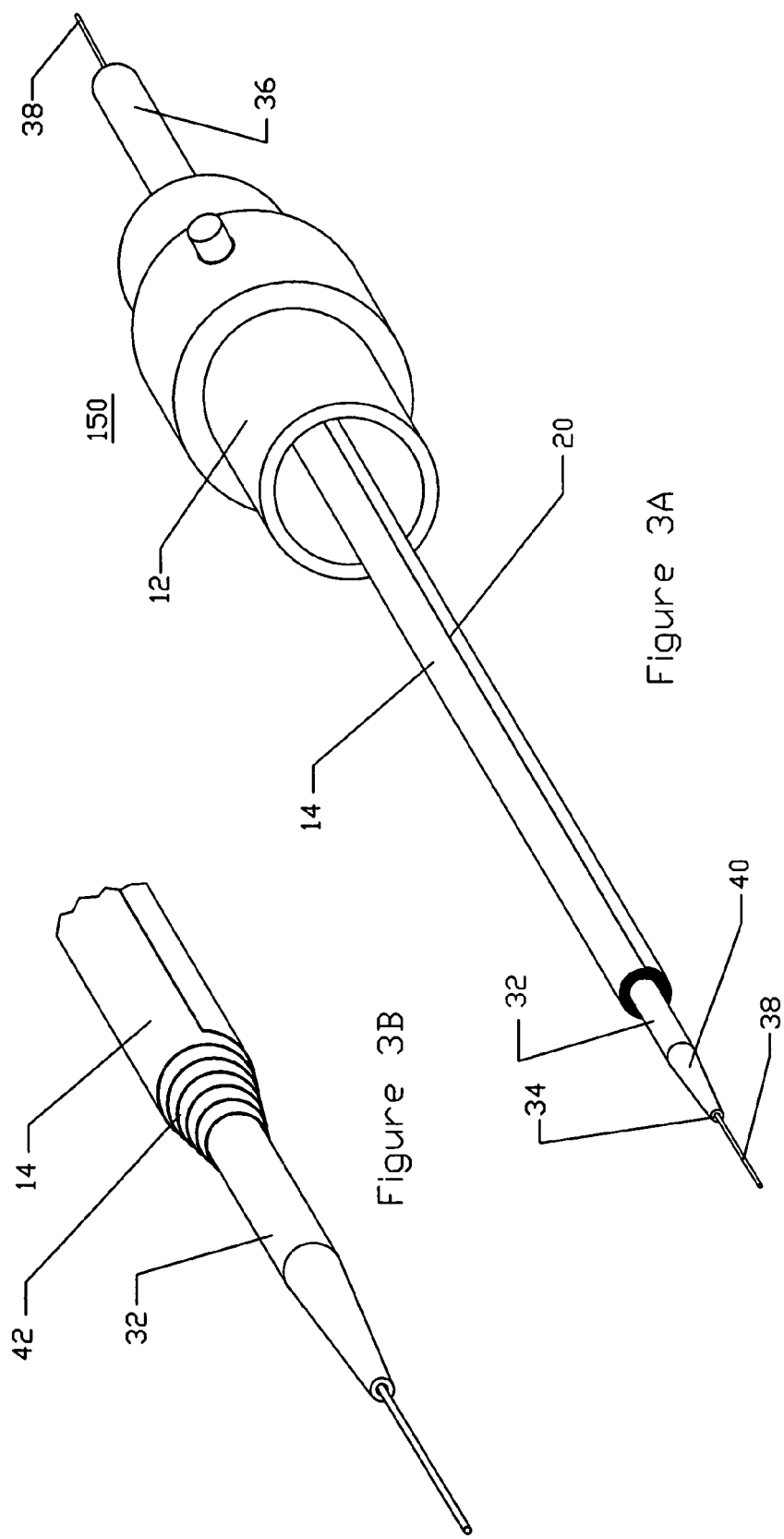
FIG. 3A is a side perspective view of another embodiment of an access sheath in a compressed or reduced profile configuration with an obturator.
FIG. 3B is a closer view of a modified embodiment of the distal end of the sheath of FIG. 3A.

FIG. 3A illustrates another embodiment of an access system 150 wherein like numbers are used to refer to parts similar to those of FIGS. 1A-2B. In this embodiment, the access system 150 includes a guidewire 28 and an obturator 32 inserted through the central lumen 30 (not shown) of the sheath 10. In the illustrated embodiment, the obturator 32 comprises a tapered tip 40 located at the distal end of the obturator 32 and an obturator handle 36 located at the proximal end of the obturator 32. The obturator 32 further comprises a guidewire lumen 34, which is a through lumen traverses the entire length of the obturator 32 from the proximal end to the distal end. A Tuohy-Borst fitting (not shown) is preferably affixed proximal to the obturator handle 36 to provide a seal for the guidewire 38 to prevent the loss of fluid from the body through the guidewire lumen 34. In certain embodiments, the diameter of the guidewire lumen 34 ranges from 0.005 to 0.100 inches and preferably between 0.010 inches to 0.050 inches. Typical guidewires 38 appropriate for this application are 0.028 to 0.038 inches in diameter.

The obturator 32 is preferably removable through the proximal end of the sheath 10 and is inserted to aid in introduction of the sheath 10 into the patient. The obturator 32 is typically used in the radially compressed configuration of the sheath 10. In one embodiment, the lateral cross-section of the obturator 32 is configured with an indent to prevent or eliminate interference between the obturator 32 and the torque member or cam 18. The obturator 32 may be formed from any of a variety of suitable materials as, but not limited to, Acrilonitrile Butadiene Styrene (ABS), polyvinyl chloride (PVC), polyethylene, polypropylene, and the like.

In a further embodiment, the access system 150 comprises a tapered telescoping configuration of the tubular sheath 14 that would follow a guidewire placed with a Seldinger method. Once adequate distal position is achieved, the telescopic elements would retract to permit even, circumferential expansion of the device. Such an embodiment of the expandable sheath 10 is especially useful for orthopedic and spinal access cases.

For example, FIG. 3B shows another embodiment of the sheath 10, wherein the thin wall wound tube 14 is fabricated from a flat piece of material that has its distal edge 42 cut at a sloping angle. Referring to FIG. 3B, the longest longitudinally oriented edge of the thin wall wound tube material 15 becomes the interior edge 22 while the shortest longitudinally oriented edge of the thin wall wound tube 14 becomes the outer edge 20. When wrapped in a tight spiral, the distal edge 42 of the thin wall wound tube 14 forms a stepped taper with each step having a height equal to the wall thickness of the thin wall wound tube 14. This tapering configuration at the distal end of the thin wall rolled or wound tube 14 permits improved insertion into the body, especially over an obturator 32 with reduced trauma and reduced force to insert.

Figure 4:
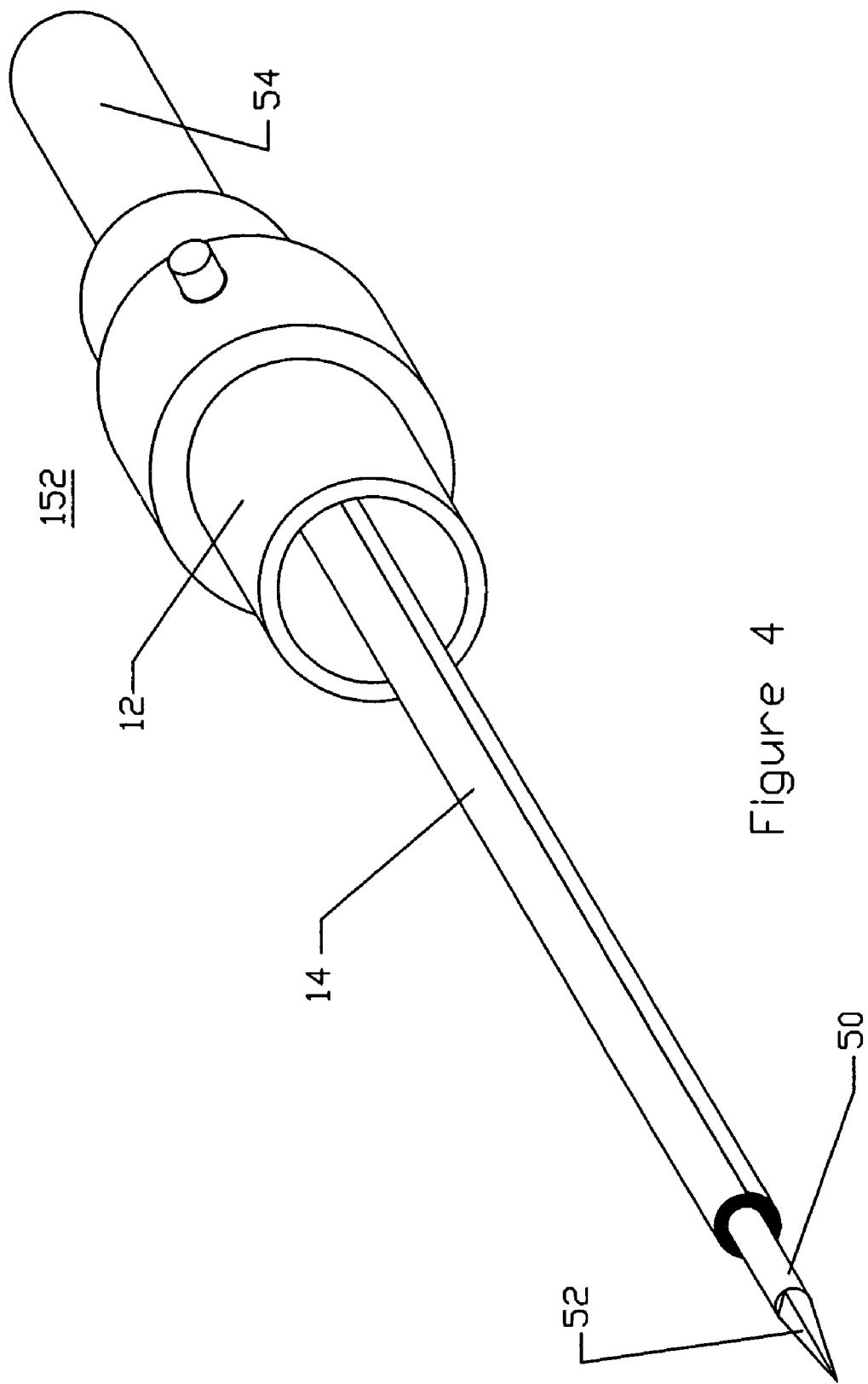
FIG. 4 is a side perspective view of another embodiment of an access sheath with a laparoscopic trocar inserted therethrough.

FIG. 4 illustrates another embodiment of an access system 152 wherein in like numbers are used to refer to parts similar to those of FIGS. 1A-2B. In this embodiment, the system 102 includes a trocar 50 inserted through the central lumen 30 of the sheath 10. The trocar 50 further comprises a sharp tip 52 located at the distal end of the trocar 50 and a trocar handle 54 located at the proximal end of the trocar 50. The trocar 50 is a device well known in the art of laparoscopic surgery and is typically made from stainless steel and polymeric materials, which include those used to fabricate the hub 12 of FIG. 1A.

Figure 5:
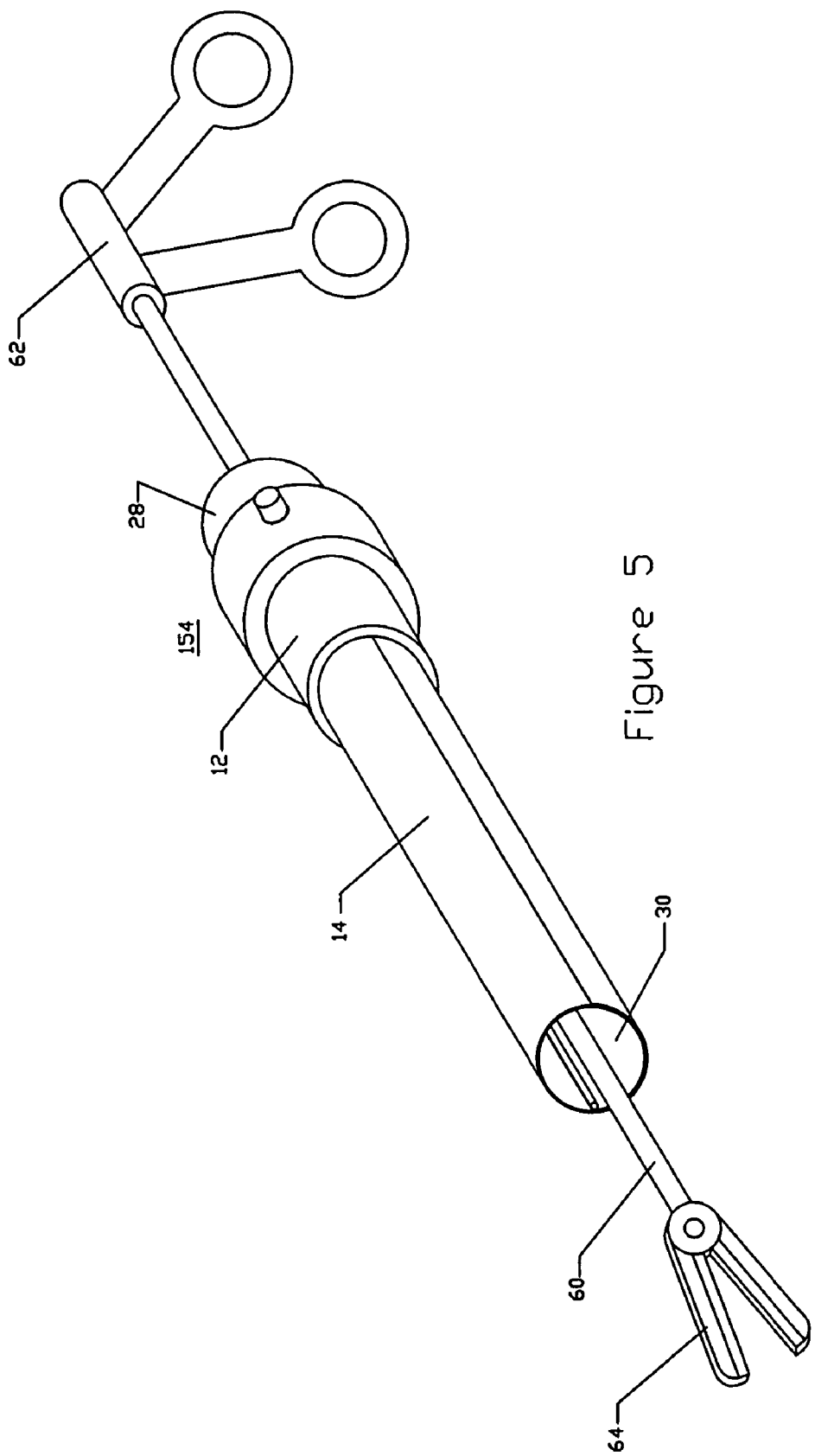
FIG. 5 is a side perspective view of another embodiment of an access sheath in an expanded configuration with a surgical instrument inserted therethrough.

FIG. 5 illustrates another embodiment of an access system 154 wherein in like numbers are used to refer to parts similar to those of FIGS. 1A-2B. In this embodiment, the system 104 comprises a grasper 60 inserted through the central lumen 30 of the sheath 10. The grasper 60 further comprises a pair of jaws 64 located at the distal end of the grasper 60 and a grasper handle 62 located at the proximal end of the grasper 60. The grasper 60 is a device well known in the art of surgery and is typically made from stainless steel, titanium, or the like. The grasper 60 is a surgical instrument and is shown as exemplary of the type of instruments that may be passed through the central lumen 30 of the expandable sheath 10. Referring to FIG. 1A and FIG. 5, the central region of the grasper 60 preferably passes through and provides a sliding seal against the seal 28, which prevents fluids, including gasses and liquids, from escaping the sheath 10. The seal 28 as described in FIG. 1A preferably has a central hole that accepts and seals to a single axially elongate smooth instrument. In another embodiment, the seal 28 has more than one hole so that more than one instrument can be inserted therethrough and seal to the seal 28. For example, a grasper 60 can be inserted through a two-hole seal 28 along with a lens or scope to visualize the procedure. Such multiple instruments placed through a single sheath are an advantage of the expandable sheath 10. The large diameter, expanded expandable sheath 10 is capable of holding two or even more instruments. In yet another embodiment, the seal 28 is omitted to allow for a more direct surgical access to the sheath 10.

Figure 6:
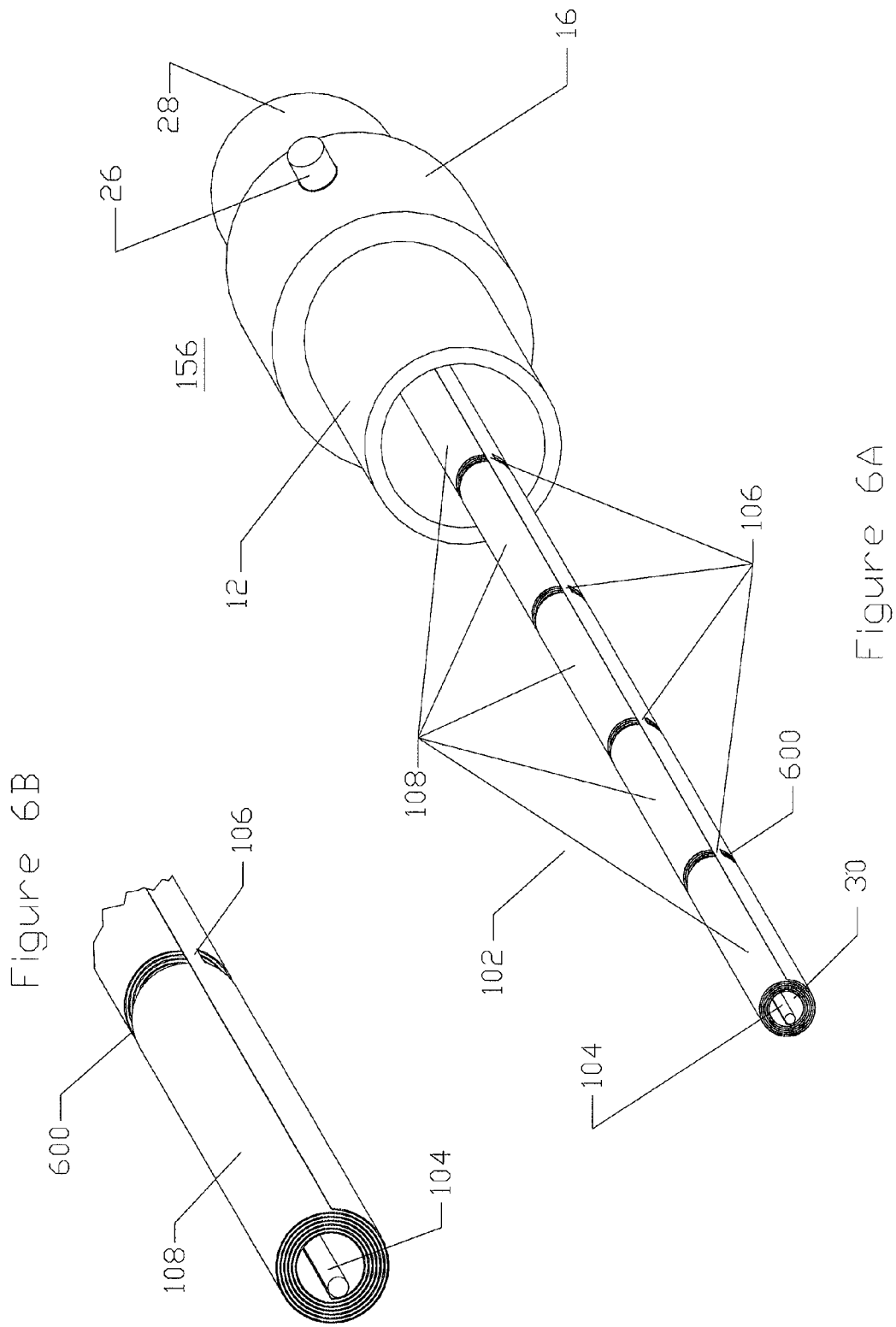
FIG. 6 are side perspective views of another embodiment of an access sheath.

FIGS. 6A and B illustrate another embodiment of an access system 156 wherein in like numbers are used to refer to parts similar to those of FIGS. 1A-2B. In this embodiment, the system the tubular sheath 14 is formed is thin wall wrapped tube 102 and a flexible torque member 104. The thin wall wrapped tube 102 further comprises a plurality of segments 108 and a plurality of axial connectors 106. FIG. 6 shows a sheath 100 comprising five segments 108. However, the sheath 100 may have any number of segments 108 from 2 to 1,000 and preferably from 4 to 20. The exterior edge of the thin material forming each segment 108 is connected to adjacent segments by an axial connector 106. The axial connectors 106 transmit torque along the length of the sheath 102 to generate a force against which the torque member 104 pushes or pulls to generate an unfurling or furling of the sheath 102 material. Referring to FIGS. 1A and 6, the articulating thin wall wrapped tube 102 is fabricated similarly to the thin wall wound tube 14 except that it is discontinuous and forms a plurality of separate spiral segments 108. This configuration results in a flexible, longitudinally separated sheath tube 102 having the configuration of an axially elongate segmented cylinder that is wound into a tight coil in its radially compressed state. Materials selected for fabrication of the sheath 100 are the same as those used for the sheath 10 embodiment shown in FIG. 1A.

In this illustrated embodiment, an operating flexible cam or torque member 104 attaches along the length of the longitudinal borders of the disjointed sheath segments 108. The flexible cam or torque member 104 is of adequate composition to transmit rotational energy uniformly over the length of the device to control the winding and unwinding if the device at the operator's discretion. The flexible cam or torque member 104 of this embodiment retains torqueability but is longitudinally flexible and capable of bending. The flexible torque member 104 in this embodiment is fabricated from materials such as PEBAX, polyethylene, polypropylene, or polyamide, preferably further comprising a braided or coiled reinforcement of materials such as, but not limited to, stainless steel, titanium, nitinol, or the like. The flexible torque member 104 may further be fabricated from metals such as stainless steel, cobalt nickel alloys, titanium, and the like but further comprise a locking spine that permits circumferential transmission of force but allows bending of the torque member 104 out of the primary longitudinal axis. The flexible cam or toque member 104 is affixed along the interior longitudinal edge of each of the sheath tube segments 108 by welding, fasteners, adhesives, or the like. The flexible torque member 104 constrains the sheath tube segments 108 from relative movement in the axial direction but the flexibility of the torque member 104 permits bending of the segments 108 in a direction out of the main longitudinal axis of the sheath 100. The flexible cam or torque member 104 is affixed to the winding knob 16 at the proximal end of the sheath 100 and rotates with the winding knob 16.

Figure 7:
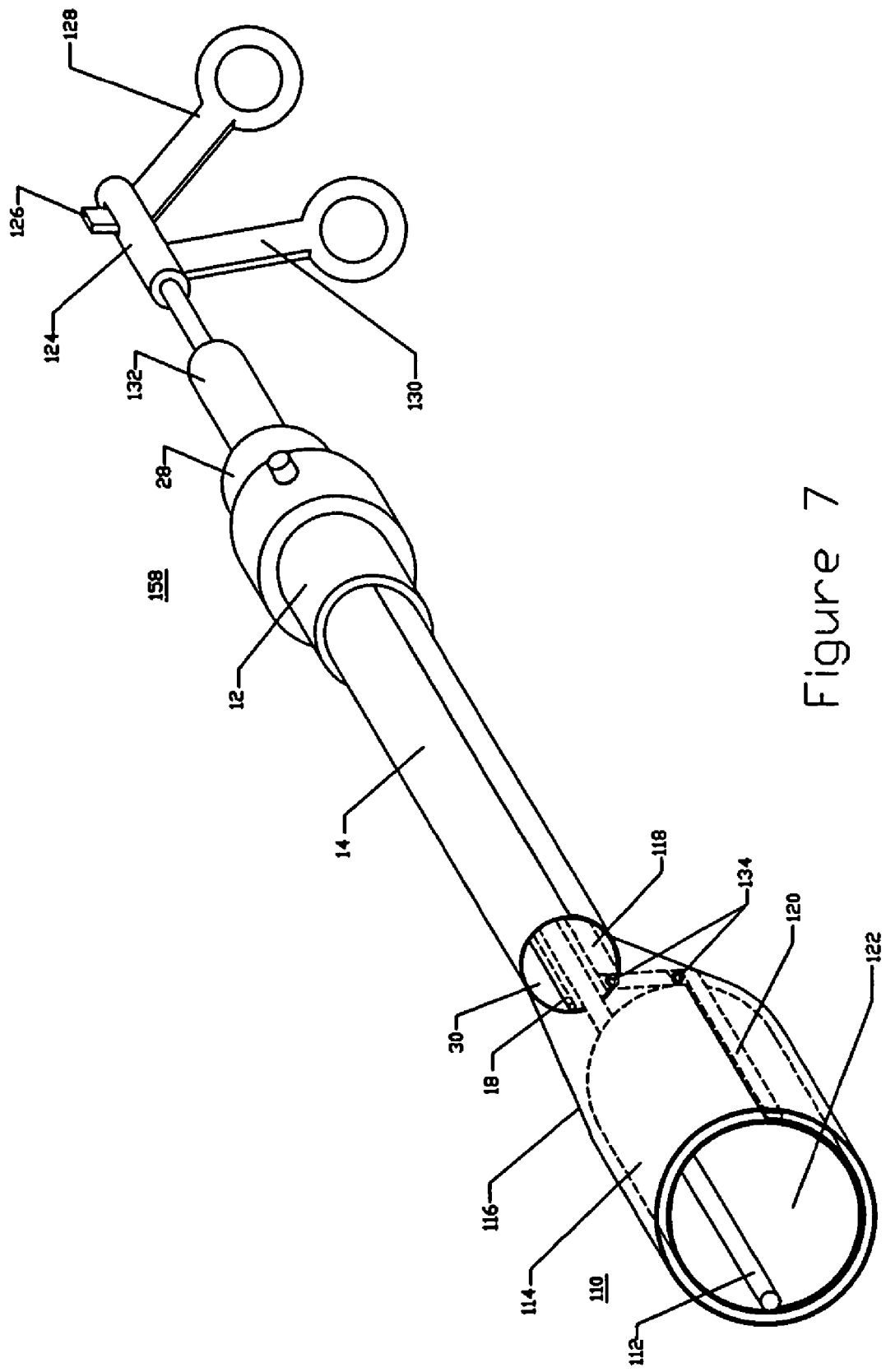
FIG. 7 is a side perspective view of another embodiment of an access sheath.

FIG. 7 illustrates another embodiment of an access system 158 wherein in like numbers are used to refer to parts similar to those of FIGS. 1A-2B. In this embodiment, the system 158 includes a dome instrument 110 expanded at the distal end of the tubular sheath 14. The dome instrument 110 is configured to surround an organ or tissue and permit therapy or removal of that tissue or organ. The dome instrument 110, in the embodiment shown in FIG. 7, is expanded the same way as the tubular sheath 14 described above. In other embodiments, the dome instrument 110 may be expanded using devices such as, but not limited to, balloon structures, expandable braids or meshes according to the teachings of U.S. Pat. No. 5,460,170 to Julius G. Hammerslag, the entirety of which is incorporated herein by reference and included as part of this specification. In the illustrated embodiment, the dome instrument 110 further comprises a dome torque member 112, a spiral wall 114, a containment layer 116, a control member 118, an external stabilizer bar 120, a dome lumen 122, a dome tool handle 124, a reverse switch 126, a dome tool rear lever 128, a dome tool front lever 130, and a dome tool hub 132. The sheath 10 further comprises the sheath hub 12, the thin wall wound tube 14, the sheath seal 28, the sheath torque member 18, and the sheath inner lumen 30.

With continued reference to FIG. 7, in the illustrated embodiment, the dome torque member 112 is coupled at its distal end to the inner portion of the dome thin spiral wall 114. The proximal end of the dome torque member 112 is rotatably affixed to the dome tool handle 124. The dome tool handle 124 is affixed to the dome tool hub 132, which is slidably inserted through the sheath seal 28. The control member 118 is affixed to the dome tool hub 132 so that it does not move either in rotation or translation relative to the dome tool hub 132. Thus, the dome torque member 112 rotates relative to the control member 118. The control member 118 is coupled at its distal end to the external stabilizer bar 120 with a hinge 134 that permits the external stabilizer bar to move radially away from the control member 118 while remaining stationary with respect to circumferential position. The external stabilizer bar 120 is coupled to the outer edge of the dome thin spiral wall 114 and preferably remains parallel to the dome torque member 112. The hinge 134 that connects the external stabilizer bar 120 to the control member 118 is preferably a double hinge arrangement to facilitate the external stabilizer bar 120 remaining parallel to the dome torque member 112. The external stabilizer bar 120 works in opposition to the dome torque member 112 to provide a counter force so that the dome thin spiral wall 114 can be unfurled larger or furled smaller in diameter. Referring to FIGS. 1A and 7, the external stabilizer bar 120 could be added an optional component of the sheath 10 and would transmit stabilization forces between the hub and the working length of the rolled thin wall sheet 14.

The containment layer 116 is preferably an elastic or unfurling inelastic membrane that completely surrounds the dome thin spiral wall 114 and which seals to the sheath thin wall wrap 14 to prevent the escape of fluids or contaminants from the dome lumen 122 or the sheath central lumen 30. The containment layer 116 expands with the dome thin spiral wall 114 and contracts, actively if it is elastomeric, or passively if it is furled, when the dome thin spiral wall 114 is contracted radially. In another embodiment, the distal edge of the dome thin spiral wall 114 is configured to be atraumatic to tissues against which it may be pressed. The atraumatic edge of the dome thin spiral wall 114 is preferably created by folding the containment layer over the distal edge of the dome thin spiral wall 114. The atraumatic edge may also be created by the addition of a bead of soft material such as silicone elastomer or polyurethane. The distal atraumatic edge of the dome thin spiral wall 114 may also be configured by putting an edge radius, a fold, or a bend in the material of the dome thin spiral wall 114 at its distal edge.

The invention described above may be embodied in other specific forms. For example, the sheath 10 or 100 may include instruments affixed integrally to the interior central lumen 30, rather than being separately inserted, for performing therapeutic or diagnostic functions. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

As described above, the access sheath may comprise an axially elongate structure having a proximal end and a distal end. The axially elongate structure further has a longitudinal axis. As is commonly used in the art of medical devices, the proximal end of the device is that end that is closest to the user, typically a surgeon. The distal end of the device is that end is closest to the patient or is first inserted into the patient. A direction being described as being proximal to a certain landmark will be closer to the surgeon, along the longitudinal axis, and further from the patient than the specified landmark. A direction that is defined as being anatomically proximal is closer to the heart and further from the exterior of the patient. A direction that is defined as being anatomically distal is further from the heart and closer to the exterior of the patient. Anatomically proximal and distal are often the opposite of being proximal and distal as defined relative to a surgical or endoluminal instrument and are defined as such for the purposes of this disclosure.

It also should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, it is contemplated that various combination or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, as mentioned above, it is intended that the scope of the present invention herein disclosed should not be limited by the particular disclosed embodiments described above, but should be determined only by a fair reading of the claims that follow

What is claimed is:

1. An access sheath adapted for providing minimally invasive surgical access, comprising:
    a tubular member formed from a rolled sheet of thin walled material, the thin walled material including an inner surface, an outer surface, an inner portion including an inner edge and an outer portion including an outer edge;
    a first component comprising a longitudinal member, the longitudinal member coupled to the inner portion of the thin walled material;
    a second component comprising a static rod coupled to the outer portion of the thin walled material and a tubular hub immovably coupled to the proximal end of the static rod; and
    a knob attached to the longitudinal member of the first component, the knob configured to rotate the first component with respect to the second component, wherein rotation of the first component with respect to the second component uniformly unwinds the rolled sheet of thin walled material of the tubular member from a first configuration comprising a lumen of uniform diameter within overlapping layers of the thin walled material to a second configuration comprising a lumen of greater uniform diameter within fewer overlapping layers of the thin walled material.

2. The access sheath of claim 1, further comprising a containment layer positioned on the outside of the rolled sheet.

3. The access sheath of claim 1, further comprising a containment layer positioned on the inside of the rolled sheet.

4. The access sheath of claim 1 further comprising a seal at a proximal end of the tubular hub.

5. The access sheath of claim 1 further comprising a lock configured to constrain the rotation of said knob with respect to said tubular hub.

6. The access sheath of claim 5 wherein the lock is a ratchet mechanism.

7. The access sheath of claim 1 wherein said second configuration comprises at least two overlapping layers.

8. The access sheath of claim 1 wherein reverse rotation of the first component with respect to the second component winds the rolled sheet of thin walled material of the tubular member from said second configuration to said first configuration.

9. The access sheath of claim 1 further comprising a removable obturator.

10. The access sheath of claim 9, wherein the removable obturator comprises a guidewire lumen extending from the proximal end to the distal end of the obturator.

11. An access sheath adapted for providing minimally invasive surgical access to a body, comprising:
    a tubular member formed from a rolled sheet, the rolled sheet comprising axially distributed segmented sections of thin walled material coupled together by connectors, each of the segmented sections of the thin walled material including an inner surface, an outer surface, an inner portion including an inner edge and an outer portion including an outer edge;
    a first component comprising a flexible longitudinal member, the flexible longitudinal member coupled to the inner portions of each of the segmented sections of the thin walled material;
    a second component comprising a static rod coupled to the outer portions of each of the segmented sections of the thin walled material and a tubular hub coupled to the proximal end of the static rod; and
    a winding knob attached to the longitudinal member of the first component, the winding knob configured to rotate the longitudinal member with respect to the static rod, wherein rotation of the longitudinal member with respect to the static rod unwinds the rolled sheet of thin walled material of the tubular member from a first configuration comprising overlapping layers of the thin walled material to a second configuration comprising fewer overlapping layers of the thin walled material.

* * * * *

UNITED STATES PATENT AND TRADEMARK OFFICE
CERTIFICATE OF CORRECTION

PATENT NO. : 7,699,864 B2 Page 1 of 1
APPLICATION NO. : 10/841799
DATED : April 20, 2010
INVENTOR(S) : George F. Kick et al.

It is certified that error appears in the above-identified patent and that said Letters Patent is hereby corrected as shown below:

On the Title Page:
(Item 75) Inventors, line 3, Change "Calrsbad," for Onnik Tchulluian to --Carlsbad,--.

In Sheet 8 of 10 (FIGURE 8B), line 4 (Approx.) Change " ∕ " to -- 21 ∕ --.

In column 1, line 23, Change "laprascopic" to --laparoscopic--.

In column 3, line 64, Change "FIG." to --FIGS.--.

In column 3, line 67, Change "sheath." to --sheath;--.

In column 4, line 13, Change "10A," to --10A.--.

In column 4, line 59, Change "to the to the" to --to the--.

In column 4, line 67, Change "outer an inner" to --outer and inner--.

In column 6, line 11, Change "gears" to --gear--.

In column 8, line 30, Change "Acrilonitrile" to --Acrylonitrile--.

In column 10, line 8, Change "deploy" to --deployed--.

In column 11, line 20, Change "Acrilonitrile" to --Acrylonitrile--.

In column 14, line 67, Change "follow" to --follow.--.

Signed and Sealed this

Seventh Day of September, 2010

David J. Kappos
*Director of the United States Patent and Trademark Office*